United States Patent [19]
Casey et al.

[11] Patent Number: 5,175,754
[45] Date of Patent: Dec. 29, 1992

[54] GANTRY POSITION REFERENCE FOR TOMOGRAPHIC SCANNERS

[75] Inventors: Colin J. Casey, West Lafayette, Ind.; Russell W. Hum, Waukesha; Phil E. Pearson, Pewaukee, both of Wis.; Judith A. Clifford, Temple Terrace, Fla.; Harold Dalman, Brookfield, Wis.

[73] Assignee: General Electric Company, Milwaukee, Wis.

[21] Appl. No.: 880,833

[22] Filed: May 11, 1992

[51] Int. Cl.[5] ............................................. H05G 1/66
[52] U.S. Cl. ........................................ 378/4; 378/94; 378/15; 378/101
[58] Field of Search ................. 378/4, 15, 94, 91, 101, 378/96, 97, 108, 110, 112, 111; 364/413.13, 413.16

[56] References Cited

U.S. PATENT DOCUMENTS 4,620,313 10/1986 Erker ....................................... 378/4

Primary Examiner—Constantine Hannaher
Assistant Examiner—Don Wong
Attorney, Agent, or Firm—Quarles & Brady

[57] ABSTRACT

A CT apparatus produces a trigger position signal having a programmable angular spacing, for triggering the acquisition of projections, from an encoder index pulse having a different fixed angular spacing. An estimation circuit estimates the time of occurrence of a next pulse in the trigger position signal by evaluating the timing of the encoder index pulses. The estimation circuit may be a phase-locked-loop or a set of lookup tables keyed to gantry position and speed.

9 Claims, 3 Drawing Sheets

GANTRY POSITION REFERENCE FOR TOMOGRAPHIC SCANNERS

BACKGROUND OF THE INVENTION

This invention relates to tomographic imaging systems such as those used for x-ray computed tomography (CT) and specifically to a tomographic system providing a gantry reference signal with adjustable spatial periodicity.

Tomographic imaging equipment produces images of transverse "slices" of an imaged object, by collecting radiation in a series of projections at various angles about the patient. The radiation may be from an extrinsic source, such as an x-ray tube positioned outside the imaged object, as in x-ray CT systems, or may be from an intrinsic source such as an ingested radioisotope, as in positron emission tomography (PET). In both cases, the data of a number of such projections is "reconstructed" to produce the slice image. The reconstruction algorithms require accurate knowledge of the "angle" at which each projection was acquired.

In a "third" or "fourth" generation CT system, for example, an x-ray source is collimated to form a fan beam with a defined fan beam angle. The fan beam is oriented to lie within the x-y plane of a Cartesian coordinate system, termed the "imaging plane", and to be transmitted through an imaged object to an x-ray detector array oriented within the imaging plane.

The detector array is comprised of detector elements each of which measures the intensity of transmitted radiation along a beam projected from the x-ray source to the particular detector element. The intensity of the transmitted radiation is dependent on the attenuation of the x-ray beam along that ray by the imaged object.

The x-ray source is rotated on a gantry within the imaging plane and around the imaged object so that the angle at which the center of the fan beam intersects the imaged object may be changed. At a number of predetermined angles, termed "trigger positions", and as determined by a rotary encoder attached to the gantry, a projection is acquired comprised of the intensity signals from each of the detector elements. Together, the projections make up a projection set.

The acquired tomographic projection set is typically stored in numerical form for computer processing to later "reconstruct" a slice image according to reconstruction algorithms known in the art. The projection set may be reconstructed directly into an image by means of fan beam reconstruction techniques, or the intensity data of the constituent projections may be sorted into parallel beams and reconstructed according to parallel beam reconstruction techniques. In either case, the reconstruction algorithms require that the angle of the gantry at which each projection was acquired be accurate.

The reconstructed tomographic images may be displayed on a conventional CRT or may be converted to a film record by means of a computer controlled camera.

The quality of the tomographic image will depend in part on the number of projections acquired Often a lower resolution may be acceptable when faster scanning speed is desired For example, a commercial CT machine may take up to 7872 projections per revolution during a single eight second revolution of the gantry. At a rotational speed of one revolution every two seconds, the data acquisition chain will permit the acquisition of only 1968 projections. The resultant lower resolution image produced by these fewer samples may be acceptable in some circumstances, such as in imaging a moving organ, where the elimination of motion induced blurring is an important consideration.

The projections are equally spaced, in angle, during the rotation of the gantry. Thus, the angular separation between the projections differs for different scan speeds. For the eight second scan described above, the angular separation between each projection will be approximately 0.05 degrees whereas in the two second scan the angular separation between projections will be approximately 0.18 degrees.

The angular spacing between projections is controlled by a rotary encoder or resolver attached to the gantry and having a very fine angular resolution, such as 0.015 degrees. Typically, a counter is used to count the encoder pulses to produce a projection acquisition signal triggering each projection. For this reason, the angular spacing of the projections for all scanning speeds must be an integer multiple of this resolution.

As mentioned, the projections are taken at equal angular spacing and thus have a constant "spatial periodicity". It should be noted however, that the projections are not spaced evenly in time, that is they do not have a constant "temporal periodicity". The reason for this is that the gantry does not rotate uniformly but tends to speed up and slow down as a result of gravitational acceleration acting on the gantry's uneven distribution of mass. Also, certain techniques, such as those used to image the heart, intentionally adjust the rotational speed of the gantry during the collection of the projection set to synchronize the acquisition of projections with the beating of the heart.

While the above described technique of using a high resolution angular encoder, and dividing its output to produce the projection acquisition signal, has the advantage of being indifferent to the speed of the gantry rotation, and thus of providing a constant spatial periodicity despite variations in the encoder signal's temporal periodicity, it also has several disadvantages. First, with practicable encoder angular resolutions, the gradation in achievable spatial periodicity of the projection acquisition signals is relatively coarse. This means that certain scan rates may not be used and the operator's flexibility in trading off resolution for speed is severely limited.

Second, projection acquisition signals having spatial periodicities that are not integer multiples of the encoder's spatial periodicity are not obtainable. Dividing the encoder signal by using a counter effectively allows only integer divisors and any implicit remainder after one gantry rotation will result in the projection acquisition signals undesirably migrating in absolute angular position between gantry rotations.

Improved CT systems of the future may permit the use of greater numbers of projections in each projection set. Such improvement is likely to be incremental, however, and thus the required projection acquisition signal may not be integer multiples of the previous encoder rate. Thus, currently, upgrades of existing machines will require replacement of the entire encoder system.

Also, for certain advanced techniques such as "spot wobble", where the focal spot of the x-ray tube is shifted back and forth during rotation of the gantry, as described in co-pending application Ser. No. 07/540,995, entitled COMPUTED TOMOGRAPHY SYSTEM WITH TRANSLATABLE FOCAL SPOT, and incorporated herein by reference, it has been discovered that an optimal spatial periodicity exists dependent on the specific geometry of the system, and that in general, this spatial periodicity will not be an integer multiple of the encoder spatial periodicity. Thus, spot wobble techniques may require additional separate encoder systems.

Accordingly, a method of providing an arbitrary acquisition signal of constant spatial periodicity, independent of a particular encoder frequency would be desirable.

SUMMARY OF THE INVENTION

The present invention relates to a method and apparatus for providing a projection acquisition signal with a constant spatial periodicity that is not an integer multiple of the encoder signal.

The invention employs a rotary encoder attached to the gantry of the tomographic system and producing an angle signal with a first constant spatial periodicity. This angle signal is received by a time estimation circuit which produces an acquisition signal also having a constant spatial periodicity but one which is different from the spatial periodicity of the encoder. The time estimation circuit works by evaluating the time of the pulses of the angle signal and from these times, estimating the time of the next pulse of the acquisition signal. By properly evaluating the time of the encoder pulses, acquisition signal pulses with a constant spatial periodicity may be generated.

The time estimation circuit may be a phase-locked-loop, which uses feedback techniques to fit a free running oscillator to a multiple of the frequency of the encoder signal, or it may be a computer circuit which employs multiple look-up tables, keyed to an estimation of the gantry speed, to produce an appropriate delay in the encoder signal pulses as necessary to produce the acquisition signal pulses.

It is one object of the invention, therefore, to produce a tomographic scanner with programmable variability in the spatial periodicity of the projection acquisition signal so as to permit maximum clinical flexibility in trading image resolution for scan time and for employing new imaging techniques such as spot wobbling. Changes in the spatial periodicity of the projection acquisition signal may be realized by changing the programmable estimation parameters used by the time estimation circuit rather than by the more difficult process of physically replacing the encoder mechanism.

It is another object of the invention to produce a tomographic scanner that may be readily upgraded to produce higher resolution images without the need to replace the encoders. The ability to generate a constant spatial periodicity signal using time domain techniques allows the generation of new acquisition signals to be performed by self-contained electrical circuits that may be readily added to existing scanners to receive the signals from existing encoders.

It is yet another object of the invention to permit the use of standard and more cost effective encoders in tomographic systems when the tomographic system requires a projection acquisition signal with an spatial periodicity not equal to an integer multiple of the standard encoder. Producing a projection acquisition signal with time domain estimation techniques allows the use of standard encoders to produce acquisition signals having spatial periodicities different from those standard encoders.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
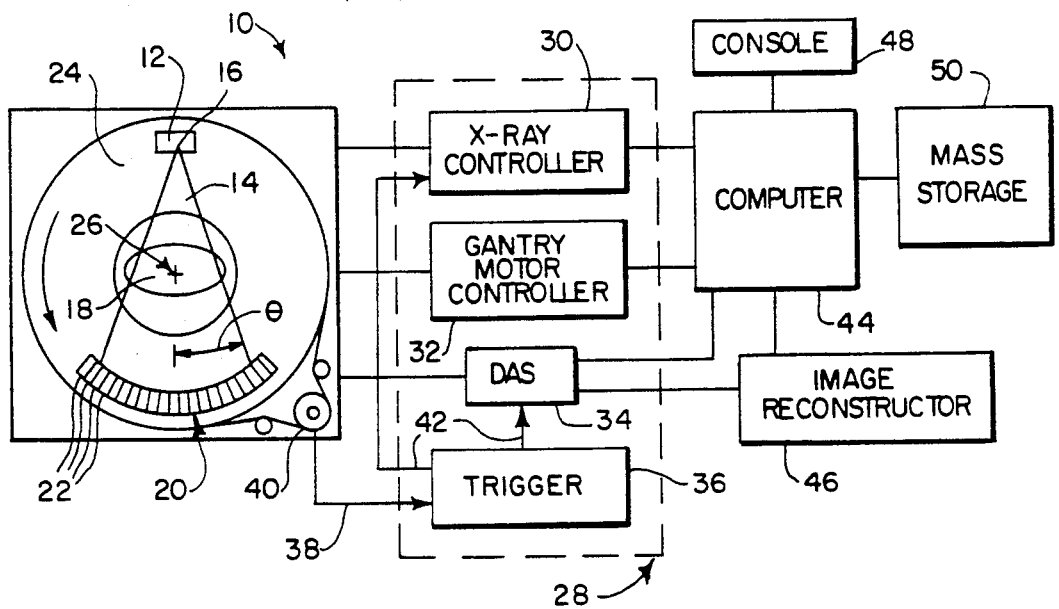
FIG. 1 is a schematic representation of a CT system suitable for use with the present invention showing an encoder and trigger.

Referring to FIG. 1, a CT system 10, representative of a "third generation" CT scanner includes an x-ray source 12 oriented to project a fan beam of x-rays 14 from a focal spot 16 through imaged object 18 to detector array 20. The detector array 20 is comprised of a number of detector elements 22 which together detect a projected image resulting from the transmission of x-rays through the imaged object 18. The angular position of the detector elements 22 about the focal spot 16 is designated 7. The x-ray source 12 and detector array 20 are mounted to a gantry 24 which rotates about a center of rotation 26 positioned near or within the imaged object 18.

The control system of a CT system 10, suitable for use with the present invention, has gantry associated control modules 28 which include: x-ray controller 30, providing power and timing signals to the x-ray source 12 and controlling the focal spot 16 position within the x-ray tube, gantry motor controller 32, which controls the rotational speed and position of the gantry 24, data acquisition system (DAS) 34, which receives projection data from the detector array 20 and converts the data to digital words for later computer processing, and trigger 36 which receives an encoder signal 38 from angular encoder 40 and produces a projection acquisition signal 42 which controls the DAS 34 and the x-ray controller 30. The encoder signal 38 is of constant spatial periodicity and the acquisition signal 42 is also of constant spatial periodicity generally different from that of the encoder signal 38. The DAS 34 receives the acquisition signal 42 to trigger the acquisition of a projection and the x-ray controller 30 receives the acquisition signal 42 to control the wobbling of the focal spot 16 with respect to the gantry 24 when the spot wobble technique is used.

The x-ray controller 30, the gantry motor controller 32 and the DAS 34 are connected to a computer 44 which may be a general purpose minicomputer such as the Data General Eclipse MV/7800C and programmed to coordinate the control and synchronization of the motion of the gantry with the acquisition of projection data according to methods understood in the art.

The computer 44 is also connected to image reconstructor 46 which receives sampled and digitized signals from the detector array 20 via the data acquisition system 34 to perform high speed image reconstruction according to the well known filtered back-projection algorithms. The image reconstructor 46 may be an array processor such as are commercially available.

The computer 44 receives commands and scanning parameters via operator console 48 which is generally a CRT display and keyboard which allows an operator to enter parameters for the scan and to display the reconstructed image and other information from the computer 44. A mass storage device 50 provides a means for storing operating programs for the CT imaging system, as well as image data for future reference by the operator.

Figure 2:
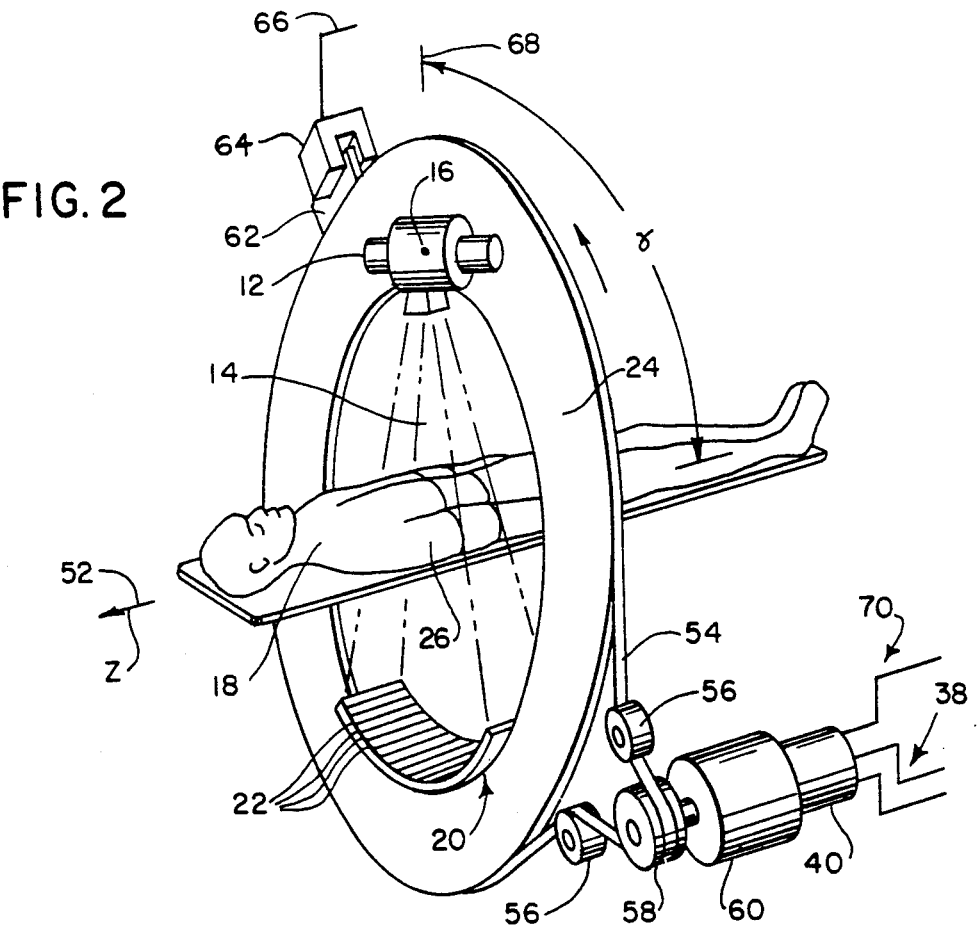
FIG. 2 is a detail of the gantry and fan beam of x-rays produced by the system of FIG. 1 showing the encoder of FIG. 1.

Referring to FIG. 2, the gantry 24 is rotated about an axis 52 passing through the center of rotation 26 and generally perpendicular to the imaging plane. The rotation of the gantry is effected by means of a belt 54 engaging the outer edge of the generally circular gantry 24 and held by means of idler pulleys 56 against a toothed sprocket 58 driven by motor 60. Encoder 40 is attached directly to the shaft of motor 60 to provide an encoder signal 38 having approximately 2,000 pulses per revolution of the motor 60 and encoder 40. The belt 54 and sprocket 58 provide for twelve revolutions of the motor 60 for every revolution of the gantry 24, and the encoder 40 produces a conventional quadrature phased digital square wave so as to provide the direction of rotation information and an effective increase in angular resolution of four. The net effect is that the encoder signal 38 divides each gantry rotation into approximately 96,000 equal angled increments. The encoder signal 38 will henceforth be considered to be the set of pulses derived from the rising and falling edges of the quadrature signals.

Attached at one point along the circumference of the gantry 24 is a flag 62 interrupting an optical sensor 64 to create a zero mark signal 66 when the gantry 24 is in a particular reference position 68. The zero mark signal 66 is used to align the encoder 40 so that an internal zero mark signal 70 generated by encoder 40 is coincident with the zero mark signal 66. Thus, the optical sensor 64 is only employed during the initial calibration of the CT system 10.

Generally, the position of the gantry 24 will be identified with respect to the reference position 68 in terms of angle $\gamma$. The encoder signal 38 as a function of $\gamma$ will be constant (constant spatial periodicity) whereas in general the encoder signal 38 as a function of time (temporal periodicity) will not be constant.

Figure 3:
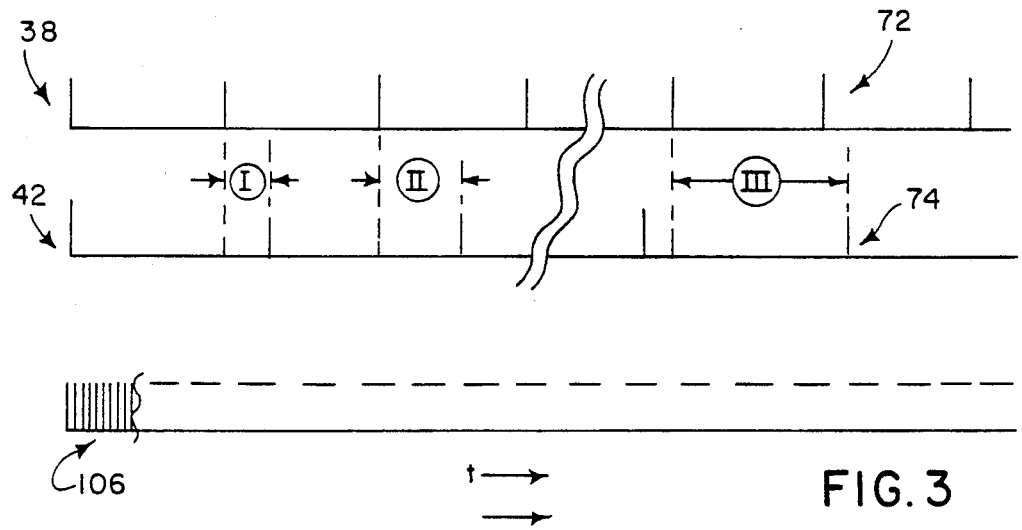
FIG. 3 is a plot of the signal from the encoder, a projection acquisition signal, which is a non-integer multiple of the encoder signal, and a clock signal, each versus time for constant angular rotation of the gantry.

Referring now to FIG. 3, the encoder signal 38 produces a set of pulses 72 equally spaced in $\gamma$ and shown equally spaced in time under the simplifying condition of constant gantry rotational speed. The trigger 36 of the present invention produces an acquisition signal 42 having pulses 74 with a different spatial periodicity than the pulses 72 of the encoder signal 38. In general, pulses 72 and 74 will align only at a single angular position of the gantry 24 at $\gamma=0$. As a result of the differing spatial periodicities of the encoder signal 38 and the acquisition signal 42, each pulse 74 of the acquisition signal 42 will occur at a varying time and angle after the previous pulse 72 of the encoder signal 38, that delay being dependent on the absolute position $\gamma$ of the gantry 24.

Figure 4:
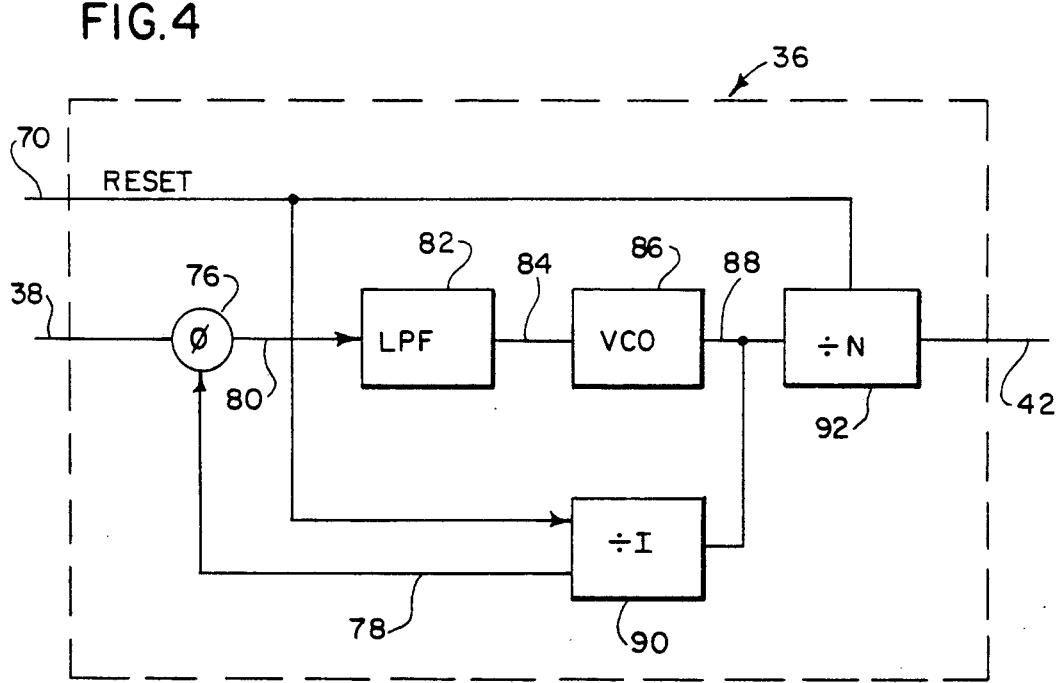
FIG. 4 is a block diagram showing one embodiment of the estimator circuit of the trigger of FIG. 1 using a phase-locked-loop.

Referring to FIG. 4, in a first embodiment, the trigger 36 is realized through the use of phase-locked-loop circuitry. The encoder signal 38 is received by a phase comparator 76 which compares the phase of the encoder signal 38 to a feedback signal 78, to be described, and produces a phase difference signal 80 functionally dependent on the magnitude and direction of the phase error between signals 38 and 78. The phase error signal 80 is received by a low pass filter 82 producing a slowly varying control voltage 84 which is received by the input of a voltage controlled oscillator 86. The voltage controlled oscillator 86 produces a digital square wave 88 having a frequency proportional to the control voltage 84. Thus, generally, if the phase of the encoder signal 38 is more advanced than the phase of the feedback signal 78, the phase comparator 76 operates to increase the control voltage 84 thus increasing the frequency of the output of the voltage controlled oscillator 86. Conversely, if the phase of the encoder signal 38 is retarded with respect to the phase of the feedback signal 78, the phase comparator 76 creates a control voltage 84 decreasing the frequency of the voltage controlled oscillator 86. It will be recognized to those of ordinary skill in the art that a variety of methods of implementing the phase comparator 76, LPF 82 and VCO 86 are possible.

The digital square wave 88 from the voltage controlled oscillator 86 is received by a programmable counter 90, which operates to divide the frequency of the digital square wave 88 by the modulus of the counter 90, which may be controlled by computer 44. Generally, counter 90 is a "divide by I" counter where I is a preselected integer. The output of the counter 90 is also the feedback signal 78, thus closing the phase-locked-loop's loop.

It will be understood that the phase-locked-loop, therefore, is a feedback system which works to match the phase of the feedback signal 78 to the phase of the encoder signal 38 according to generally understood control system theory. It will also be understood therefore, that the low pass filter 82 has characteristics, selected according to generally understood stability criteria, to insure that the phase-locked-loop operates in a responsive yet stable manner. The effective feedback frequency gain of the phase-locked-loop is 1/I and, therefore, digital square wave 88 at the output of the voltage controlled oscillator 86 has a frequency of I times that of the encoder 38.

The digital square wave 88 in turn is received by a second counter 92, similar to the first counter 90 which divides the frequency of the digital square wave 88 by N, where N is a second preselected integer. The output of counter 92 is the acquisition signal 42, which will therefore be equal in frequency to encoder signal 38 multiplied by I and divided by N. Thus, the trigger circuit 36 provides an acquisition signal 42 that is (1) locked in phase to the encoder signal 38 and yet (2) a non-integer multiple of that encoder signal 38, as dictated by the factor and divisor I and N.

The internal zero mark signal 70 is used to provide a reference to other circuitry (not shown), the reference insuring reproducibility of the absolute gantry positions between scans.

The phase-locked-loop is a time domain device, that is, its elements, specifically the voltage controlled oscillator 86, are directly responsive to time, not to the position of the gantry 24. Nevertheless, the low pass filter 82 and the voltage controlled oscillator 86 vary their signals to compensate for changes in the effective rotational speed of the gantry 24, based on the timing of the previous encoder pulses 38, and thus for most circumstances, can produce an acquisition signal 42 that has essentially constant spatial periodicity despite changes in the quantity rotation speed. Thus, the elements of the phase-locked-loop serve to estimate the time of occurrence of the next pulse 74 of the acquisition signal 42, based on the time of occurrence of previous pulses 72 from encoder signal 38 necessary to produce constant spatial periodicity.

Figure 5:
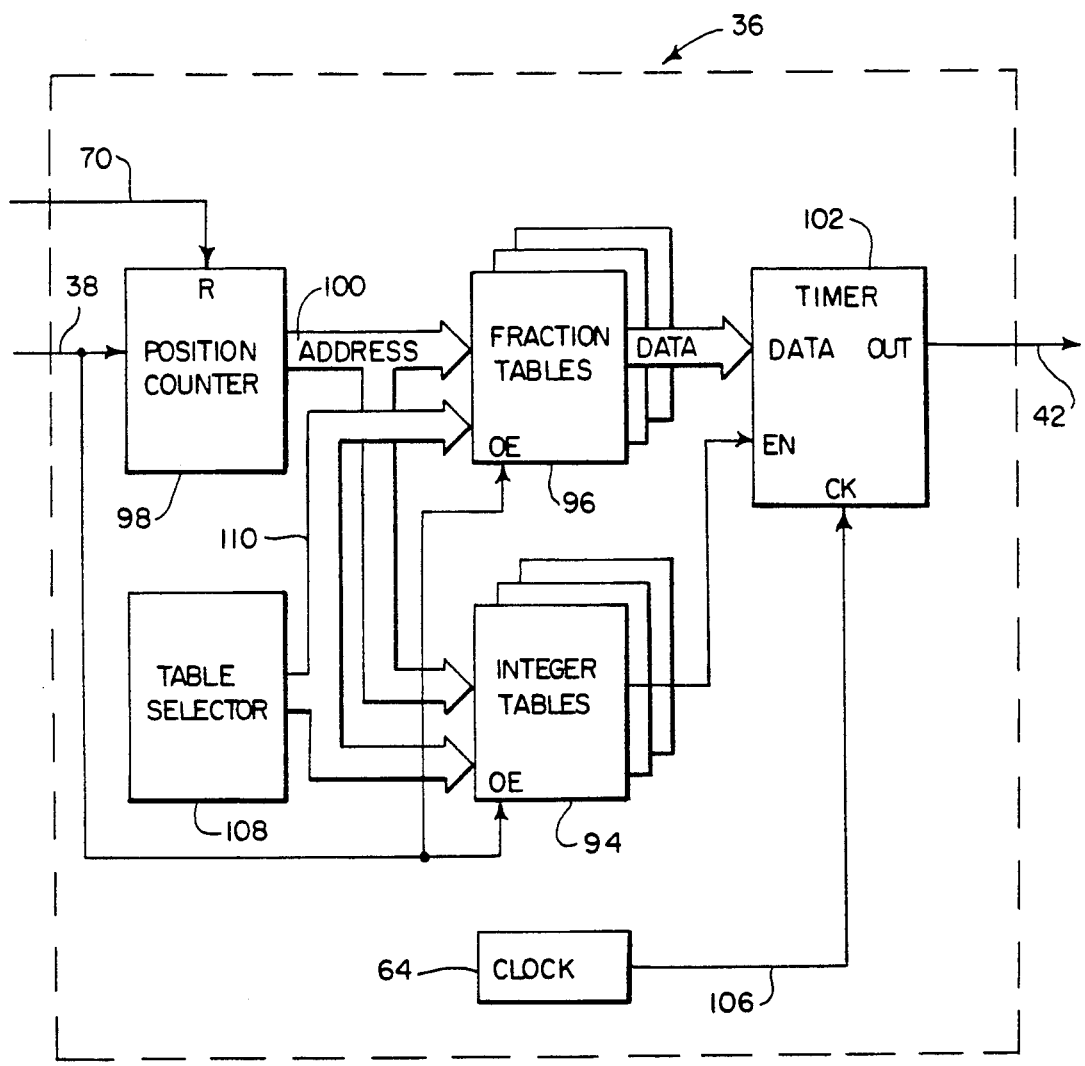
FIG. 5 is a block diagram similar to that of FIG. 4 showing a second embodiment of the estimation circuit of the trigger of FIG. 1.

Referring now to FIG. 5, in a second embodiment, the trigger circuitry 36 is realized with a set of look-up tables 94 and 96, which provide estimates of the required delay between pulses 72 of the encoder signal 38 and pulses 74 of the acquisition signal 42 for multiple quantity speeds.

Referring also to FIG. 3, it will be noted that for constant speed gantry rotation, the delay indicated by I through III will, between pulses 72 and 74, vary depending on the actual position $\gamma$ of the gantry. The dependency of the delay on the absolute position $\gamma$ of the gantry 24 requires that the position $\gamma$ of the encoder 24 be tracked. This is accomplished by position counter 98, which receives encoder signal 38 and counts pulses 72. Position counter 98 is reset by internal zero mark signal 70 to correspond with the $\gamma = 0$ position of gantry 24. It should be further noted that delays I and II involve only a fraction of the period between pulses 72 of encoder signal 38, whereas delay III is greater than the period between pulses 72 of encoder signal 38. For the most general case, the delay between these pulses will involve a fraction plus an integer times the period between pulses 72 of encoder signal 38.

The output of the position counter 98 provides a first address 100 used to obtain delay values from fraction table 96 and integer table 94, which together control a timer 102 which times the delay in pulse 74 after a previous pulse 72 of the encoder signal 38. For the delays I and II, involving a delay less than or equal to the period between pulses 72, the integer table will contain a value of zero which enables the timer 102. For delays such as III, involving a period greater than the period between pulses 72, the integer table 94 will produce a value of one, which disables the timer 102.

The fraction table 96 contains the fractional part of the delay I, II or III being the entire delay in cases I and II and being that portion of the delay III greater than the period between pulses 72. At each pulse 72 of encoder signal 38 the fraction table and integer table have their outputs enabled, providing their data to the timer 102. If the value in the integer table is one, the timer is disabled until the next pulse 72 of encoder signal 38. If the value in integer table 94 is 0, timer 102 is enabled and, having received the fraction value from fraction table 96, counts down by that amount to produce an output pulse 74 of acquisition signal 42 when the delay is complete. The delay value in fraction table 96 is simply a predetermined number of clock pulses from high speed clock 104, producing a signal 106 having a frequency much higher than either the encoder signal 38 or the acquisition signal 42. Thus, a variable time delay time by clock 104 is produced after each pulse 72 to produce the acquisition signal 42.

It will be understood that the value in the fraction table 96 and the integer table 94 will provide a fixed time delay and therefore produce an acquisition signal 42 with constant spatial periodicity only for a single, constant gantry rotational speed. Different gantry rotational speeds are accommodated by the use of multiple levels of look-up tables 96 and 94 selected according to the speed of the gantry rotation. Specifically, a table selector 1 provides a second address 110 for use in addressing the fraction table 96 and the integer table 94, the second address 110 being dependent on the speed of the gantry rotation as input by the user.

Thus, fraction table and integer table contain estimates of the time of occurrence of pulses 74 based on the previous pulses 72 which both provide a starting point for the delay values derived from the fraction and integer tables 96 and 94. The integer table contains one bit for each of the pulses 72 and the fraction table contains ten bits for each of the pulses 72. It will be understood that the number of bits in the fraction table may be increased per pulse 72 to provide additional precision in the placement of pulses 74. Calculation of the required delays contained in tables 96 and 94 is a simple recursive exercise that will be understood for those of ordinary skill in the art.

Many modifications and variations of the preferred embodiment which will still be within the spirit and scope of the invention will be apparent to those with ordinary skill in the art. In order to apprise the public of the various embodiments that may fall within the scope of the invention, the following claims are made.

I claim:

1. A tomographic imaging system for imaging a body, the system comprising:
   a gantry for moving about an axis through a plurality of angles;
   a position encoder attached to the gantry for producing a position signal with first pulses having a first constant spatial periodicity and a first variable temporal periodicity;
   an estimation means receiving the first pulses and for producing an acquisition signal with second pulses having a second constant spatial periodicity and a second temporal periodicity, by estimating the time of occurrence of a next second pulse based on the time of occurrence of at least one previous first pulse; and
   a detector system attached to the gantry for acquiring a series of projections of the body coincident with the second pulses of the acquisition signal.

2. The tomographic system as recited in claim 1 including:
   an x-ray source attached to the gantry opposite the detector for producing x-rays illuminating the imaged object and received by the detector system.

3. The tomographic system of claim 1 wherein the estimation means is a phase-locked-loop having:
   a phase comparator receiving both the previous first pulse and a feedback signal to produce a phase error signal;
   a controlled oscillator for receiving the phase error signal and for producing the next second pulse of the acquisition signal; and
   a scaler receiving the next second pulse from the controlled oscillator and for producing the feedback signal by selectively transmitting only a predetermined fraction of the next second pulses it receives.

4. The tomographic system of claim 3 wherein the scaler is a divide by I counter, wherein I is a preselected integer.

5. The tomographic system of claim 3 wherein the controlled oscillator is a voltage controlled oscillator receiving a voltage from a low-pass filter.

6. The tomographic system of claim 1 wherein the estimation means is a phase-locked-loop having:
- a phase comparator receiving both the previous first pulse and a feedback signal to produce a phase error signal;
- a controlled oscillator for receiving the phase error signal and for producing a pulse train;
- a scaler receiving the pulse train from the controlled oscillator and for producing the feedback signal by selectively transmitting only a predetermined fraction of the pulses it receives; and
- a divider receiving the pulse train from the controlled oscillator and for producing the acquisition signal by selectively transmitting only a predetermined percentage of the pulses it receives.

7. The tomographic system of claim 6 wherein the scaler is a divide by I counter, wherein I is a preselected integer.

8. The tomographic system of claim 6 wherein the controlled oscillator is a voltage controlled oscillator receiving a voltage from a low-pass filter.

9. The tomographic system of claim 1 wherein the estimation means includes:
- a counter for counting the first pulses of the angle signal to produce an absolute angle signal;
- a look-up table receiving as an address the absolute angle signal and for providing a delay time;
- a clock for providing a clock signal; and
- a timer receiving the clock signal and the delay time for producing the next second pulse at the delay time after the previous first pulse.

* * * * *